United States Patent [19]

Kuramoto et al.

[11] Patent Number: 5,470,580
[45] Date of Patent: Nov. 28, 1995

US005470580A

[54] DIRECTLY-COMPRESSIBLE NAPROXEN OR NAPROXEN SODIUM COMPOSITIONS

[75] Inventors: Roy Kuramoto, Redwood City; Zakauddin T. Chowhan, Sunnyvale; Ranal O. Pendleton, Palo Alto, all of Calif.; Hafez Hafezzadeh, Boulder, Colo.

[73] Assignee: Syntex Pharmaceuticals International Limited, Palo Alto, Calif.

[21] Appl. No.: 271,339

[22] Filed: Jul. 6, 1994

Related U.S. Application Data

[60] Division of Ser. No. 878,145, May 4, 1992, Pat. No. 5,358, 717, which is a continuation-in-part of Ser. No. 759,783, Aug. 27, 1991, abandoned, which is a continuation of Ser. No. 455,109, Dec. 22, 1989, abandoned.

[51] Int. Cl.$^6$ ................................ A61K 9/16; A61K 9/20
[52] U.S. Cl. ...................... 424/464; 424/465; 424/489; 514/960
[58] Field of Search ...................... 424/464, 465, 424/489

[56] References Cited

U.S. PATENT DOCUMENTS

| | | | |
|---|---|---|---|
| 4,009,197 | 2/1977 | Fried et al. | 260/473 F |
| 4,246,164 | 1/1981 | Felder et al. | 260/501.17 |
| 4,605,758 | 8/1986 | Schloemer | 562/418 |
| 4,710,519 | 12/1987 | Finnan et al. | 514/629 |
| 4,721,709 | 1/1988 | Seth et al. | 514/221 |
| 4,723,033 | 1/1988 | Erickson | 560/56 |
| 4,744,987 | 5/1988 | Mehra et al. | 424/256 |
| 4,753,801 | 6/1988 | Oren et al. | 424/465 |
| 4,760,094 | 7/1988 | Blank et al. | 514/629 |
| 4,904,477 | 2/1990 | Ho et al. | 424/465 |

FOREIGN PATENT DOCUMENTS 1168156  5/1984  Canada.

*Primary Examiner*—Thurman K. Page
*Assistant Examiner*—James M. Spear
*Attorney, Agent, or Firm*—Wayne W. Montgomery

[57] ABSTRACT

The present invention relates to directly-compressible naproxen or naproxen sodium compositions comprising spray-dried naproxen or naproxen sodium. The present invention further relates the processes for preparing the directly-compressible naproxen or naproxen sodium compositions, to aqueous mixtures containing naproxen or sodium naproxen suitable for spray-drying and useful in the processes for preparing the directly-compressible compositions, to naproxen or naproxen sodium tablets prepared from the directly-compressible compositions, and to the processes for preparing the naproxen or naproxen sodium tablets.

45 Claims, No Drawings

DIRECTLY-COMPRESSIBLE NAPROXEN OR NAPROXEN SODIUM COMPOSITIONS

This application is a division of Ser. No. 07/878,145, filed May 04,1992, U.S. Pat. No. 5,358,717 which is a continuation-in-part of application Ser. No. 07/759,783, filed Aug. 27, 1991, now abandoned which is a continuation of application Ser. No. 07/455,109, filed Dec. 22, 1989, which is now abandoned.

FIELD OF THE INVENTION

The present invention relates to directly-compressible pharmaceutical compositions and the processes for preparing such compositions.

BACKGROUND OF THE INVENTION

Tablet formulations of pharmaceutically active drugs are not normally comprised purely of the active ingredient. Excipient materials are usually included in tablet formulations to confer the necessary and desirable characteristics of a pharmaceutically acceptable tablet (e.g., acceptable hardness, rate of dissolution, and stability and a size and weight practical for oral administration). For example, diluents increase bulk, binders impart cohesive qualities, lubricants prevent adhesion to the surface of dies and punches during tableting operations, glidants improve flow characteristics, disintegrating agents facilitate breakup or disintegration after administration, coloring agents improve aesthetics and flavoring agents enhance palatability.

Directly-compressible drug compositions are prepared by a variety of techniques. Of the commonly employed methods, wet-granulation is the most widely used. The wet-granulation method is employed with formulations that are difficult to tablet and requires complicated steps of powder-mixing, kneading, granulation, drying, sieving and mixing.

More specifically, in wet-granulation a mixture of powdered active pharmaceutical and excipients is granulated by adding or spraying a binder solution until a wet mass is formed. The wet mass is dried, milled and then blended with a lubricant to form a directly-compressible pharmaceutical composition. This process is complicated, time-consuming, and costly.

In some instances, spray drying techniques are useful in preparing directly-compressible drug compositions. In a spray drying operation an aqueous mixture of the ingredients is atomized and passed into a chamber through which hot drying gas is circulated. The solvent rapidly evaporates and porous, uniform granules comprised of evenly distributed ingredients are recovered (e.g., see "Spray Drying Handbook" by K. Masters, Fourth Edition, Longmans/Wiley, New York, 1985).

Compositions containing spray-dried drug components can exhibit increased lubricity (e.g., see U.S. Pat. No. 4,904,477) or produce less friable tablets (e.g., see Canadian Patent 1 168 156). In some instances, spray-dried drug compositions are directly compressible into acceptable tablets (e.g., see U.S. Pat. No. 4,710,519).

Directly-compressible naproxen and naproxen sodium compositions are prepared by a wet-granulation method. Naproxen or naproxen sodium is obtained from synthesis as a wet cake or an aqueous mixture (e.g., see U.S. Pat. Nos. 4,723,033; 4,605,758; 4,246,164; and 4,009,197). The wet naproxen or naproxen sodium is dried. The dry drug is milled and then is blended with the disintegrating agent. To the dry blend is added a solution of binder to form a wet-granulation mixture of active ingredient, disintegrating agent and binder. The wet mixture is dried and milled to form a dry naproxen or naproxen sodium composition which is blended with lubricant and additional disintegrating agent to form a directly-compressible naproxen or naproxen sodium composition.

The drying and milling steps necessary in the wet-granulation of naproxen or naproxen sodium are costly in terms of energy, labor and capital equipment. A considerable advantage is realized if spray-drying techniques can be employed to eliminate such steps. However, directly-compressible compositions are not readily prepared from spray-dried naproxen or naproxen sodium compositions. Compositions comprising spray-dried naproxen or naproxen sodium may exhibit poor compressibility and compactibility characteristics or the tablets prepared therefrom may have poor dissolution characteristics.

The disclosure of these and other documents referred to throughout this application (e.g., in the Detailed Description of the Invention) are incorporated herein by reference.

SUMMARY OF THE INVENTION

A feature of the present invention is a directly-compressible naproxen or naproxen sodium composition. A directly-compressible naproxen composition consists essentially of 90 to 97% spray-dried naproxen, 0.5 to 1.5% free moisture content, 1 to 6% binder, 1 to 6% disintegrating agent, and 0.1 to 2.0% lubricant. Preferred directly-compressible naproxen compositions contain croscarmellose sodium as the disintegrating agent and povidone or hydroxypropylmethylcellulose as a binder. Most preferred directly-compressible naproxen compositions consist essentially of 92 to 96% spray-dried naproxen, 0.5 to 1.5% free moisture ,content, 3 to 5% croscarmellose sodium, 1 to 3% povidone, and 0.1 to 2.0% lubricant.

A directly-compressible naproxen sodium composition consists essentially of 80 to 90% spray-dried naproxen sodium, 6.0 to 8.0% free moisture content, 1 to 6% binder, 1 to 6% disintegrating agent, and 0.1 to 2.0% lubricant. Preferred directly-compressible naproxen sodium compositions contain croscarmellose sodium as the disintegrating agent and povidone or hydroxypropylmethylcellulose as a binder. Most preferred directly-compressible naproxen sodium compositions consist essentially of 82 to 86% spray-dried naproxen sodium, 6.0 to 8.0% free moisture content, 2 to 6% croscarmellose sodium, 1 to 4% povidone, and 0.1 to 2.0% lubricant.

A second feature of the invention is a spray-dried naproxen or naproxen sodium composition suitable to combine with dry excipients to obtain a directly-compressible naproxen or naproxen sodium composition. A spray-dried naproxen composition consists essentially of 90 to 100% naproxen, 0 to 1.63% free moisture content, 0 to 6.25% binder and 0 to 6.25% disintegrating agent. A spray-dried naproxen sodium composition consists essentially of 80 to 100% naproxen sodium, 0 to 9.09% free moisture content, 0 to 6.97% binder, and 0 to 6.97% disintegrating agent.

A third feature of the invention is an aqueous mixture comprising naproxen or naproxen sodium suitable for spray drying to obtain a spray-dried composition, which spray-dried composition is useful for preparing a directly-compressible naproxen or naproxen sodium composition. The solids of an aqueous mixture suitable for spray-drying to obtain a spray-dried naproxen composition consists essentially of 90.46 to 100% naproxen, 0 to 6.25% binder, and 0 to 6.25% disintegrating agent. The solids of an aqueous mixture suitable for spray-drying to obtain a spray-dried naproxen sodium composition consists essentially of 85.11 to 100% naproxen sodium, 0 to 6.97% binder, and 0 to 6.97% disintegrating agent.

A fourth feature of the present invention is a naproxen or naproxen sodium tablet prepared from the directly-compressible compositions of the present invention.

A fifth feature of the present invention is the processes for preparing the spray-dried naproxen or naproxen sodium compositions, the directly-compressible naproxen or naproxen sodium compositions, and the naproxen or naproxen sodium tablets of the present invention.

ADVANTAGES OF THE INVENTION

The directly-compressible naproxen or naproxen sodium compositions of the present invention are free-flowing, possess excellent compactibility and compressibility characteristics, and are exceptionally suited for compression into pharmaceutically acceptable tablets. The directly-compressible compositions are stable and can therefore be packed in moisture-proof containers and stored for periods of time prior to tableting.

The naproxen or naproxen sodium tablets prepared from the directly-compressible compositions possess acceptable hardness, are stable and have good dissolution characteristics. Because of the low levels of excipients present, the tablets are smaller and thus are more easily administered orally.

Naproxen and naproxen sodium are conveniently obtained in aqueous forms and because the process of the present invention produces an evenly blended spray-dried composition from an aqueous mixture, energy intensive drying and milling steps are eliminated.

These and other advantages and features of the present invention will become apparent to those persons skilled in the art upon reading the details of the invention as more fully set forth below.

DETAILED DESCRIPTION OF THE INVENTION

Definitions

Unless otherwise stated, the following terms as used in this specification and the appended claims have the following meanings:

All percentages refer to percentages by weight (% w/w if referring to solids or % w/v if referring to aqueous mixtures).

The singular forms "a" "an" and "the" include plural referents unless the context clearly dictates otherwise. Thus a reference to "an excipient" includes reference to mixtures of excipients or a reference to "the method of spray drying" includes one or more different methods of spray drying known to those skilled in the art.

The term "aqueous mixture" or "combined aqueous mixture" means both aqueous solutions and aqueous slurries.

The term "pharmaceutically acceptable" means that which is generally safe, non-toxic and neither biologically nor otherwise undesirable and includes that which is acceptable for veterinary use as well as human pharmaceutical use.

The term "pharmaceutically acceptable tablets" means tablets which are pharmaceutically acceptable, as defined above, and which possess the necessary and desirable characteristics of a tablet acceptable for administration to a patient (e.g., acceptable hardness, acceptable dissolution characteristics, stable, and a size and weight practical for oral administration).

The term "acceptable hardness" means an acceptable resistance to chipping, abrasion, or breakage under conditions of storage, transportation, and handling before usage, generally corresponding about to 4 to 15 units on a Strong-Cobb hardness scale (S.C. Units), preferably 5 to 6 S.C. Units.

The term "acceptable dissolution characteristics" means that when measured by Apparatus 2 (USP paddle method) 90 to 100% the drug dissolves within 30 minutes.

The term "stable" when used to describe tablets, means that under normal handling and storage conditions the tablet retains its original size, shape, weight, and the active ingredient retains good bioavailability. When used to describe pharmaceutical powders the term "stable" means that the powder retains its compactibility and compressibility characteristics and the active ingredient has good bioavailability when compressed into tablet form.

The term "free-flowing" means ease of handling as in, for example, measuring, introducing into packages, or feeding into high-speed tableting equipment.

The term "compressibility" means the degree to which a powder decreases in volume under pressure when forming a tablet.

The term "compactibility" means the ease with which a powder is compressed into tablets possessing acceptable hardness properties.

The term "free moisture content" means that proportion of a material (e.g., a composition or tablet) which is water that is lost under standard drying techniques, and excludes any water of crystallization present in any of the components of the material. The free moisture content is determined by drying the material and measuring the water lost under specified test conditions with a standard moisture analyzer (e.g., a Computrac Moisture Analyzer). The amount of water lost on drying is expressed as the percentage loss by weight of the mass of the material before drying (percent loss on drying or % LOD).

The term "spray-dried composition" means a composition prepared in a single operation by spray drying techniques. Thus, not considering the free moisture content, a spray-dried naproxen composition may consist solely of spray-dried naproxen or may consist of a spray-dried mixture of naproxen and excipients. Similarly, a spray-dried naproxen sodium composition may consist solely of spray-dried naproxen sodium or may consist of a spray-dried mixture of naproxen sodium and excipients.

The term "spray-dried naproxen" or "spray-dried naproxen sodium" means that component of a spray-dried composition which is the naproxen or naproxen sodium.

The term "directly-compressible composition" means a composition which can be, without additional process steps, compressed into a pharmaceutically acceptable tablet.

Materials

Naproxen and naproxen sodium may be prepared by methods known to those skilled in the art (e.g., see U.S. Pat. No. 4,723,033; 4,605,758; 4,246,164; and 4,009,197). Because the processes of the present invention do not require dry naproxen or naproxen sodium as a starting material, either drug may be obtained directly from the final step of its synthesis in the form of a wet cake or an aqueous slurry. Water is added when necessary, and the aqueous mixture is milled using conventional milling equipment to obtain the desired range of particle size distribution. The aqueous mixture contains 40 to 80% naproxen or naproxen sodium.

Typical excipients useful in the present invention include binders, disintegrating agents, lubricants, coloring agents, diluents, glidants, and flavoring agents.

Acceptable binders include polyvinyl resins (e.g., polyvinyl alcohol and polyvinyl pyrrolidone), water soluble derivatives of cellulose (e.g., hydroxypropylmethylcellulose and sodium carboxymethylcellulose), water soluble gums (e.g., gum acacia), starches, (e.g., pregelatinized starches), and gelatin. Combinations of binders are also useful (e.g., the combination of gelatin and polyvinyl pyrrolidone or various combinations of the binders mentioned above).

Poly-1-Vinyl-2-pyrrolidinone (Povidone USP) and hydroxypropylmethylcellulose are preferred binders. Povidone is produced commercially as a series of products with average molecular weights ranging from 10,000 to 700,000. Povidone is available in various grades referred to by K-values (e.g., K-90 corresponds to a product with an average molecular weights of 360,000). Povidone is soluble in water up to 60% and is freely soluble in many organic solvents, including monohydric alcohols (e.g., ethanol and methanol, polyhydric alcohols, acid esters, ketones, methylene chloride, chloroform). The viscosity of povidone solutions at concentrations above 10% depends on the molecular weight. Povidone of USP purity is available commercially from GAF Corporation, 1361 Alps Road, Wayne, N.J. 07470-3687 U.S.A. under the trademark PLASDONE K.A.

Hydroxypropylmethylcellulose is available commercially in grades comprised of 16.5 to 30.0% methoxy ($-OCH_3$) and 4.0 to 32.0% hydroxypropoxy ($-OCH_2CHOHCH_3$) groups, from the Dow Chemical Company under the trademark METHOCEL. The different grades of Methocel are available as Methocel E, Methocel F, Methocel J and Methocel K.

Acceptable disintegrating agents include corn and potato starch, microcrystalline cellulose, and croscarmellose sodium, preferably croscarmellose sodium. Croscarmellose sodium, an internally crosslinked form of sodium carboxymethylcellulose, is a pure, white, free flowing powder, which does not interfere with binding or flow at typical use levels. Croscarmellose sodium is essentially water insoluble, but is highly absorbent and provides excellent disintegration and dissolution properties to tablets when used at levels as low as 5%. Croscarmellose sodium is available commercially from FMC Corporation, 200 Market Street, Philadelphia Pa. 19103, U.S.A. under the Trademark Ac Di Sol.

Acceptable lubricants include magnesium stearate, stearic acid, sodium stearyl fumarate or a mixture of a lubricant with talc (glidant). Acceptable pigments include iron oxide, FD&C dyes and lakes.

Description

Naproxen or naproxen sodium, preferably in the form of a wet cake or an aqueous mixture obtained directly from the final step in the synthesis thereof, is mixed with water, if necessary, and the mixture milled using conventional milling equipment to obtain the desired range of particle size distribution. The aqueous mixture of naproxen or sodium naproxen is combined with sufficient amounts of water and optionally with acceptable excipients to constitute a combined aqueous mixture suitable for spray drying and containing 20 to 70% solids. Acceptable excipients include the binders, disintegrating agents, pigments, and lubricants described above.

The combined aqueous mixture is spray-dried by conventional methods (e.g., see "Spray Drying Handbook" by K. Masters, Fourth Edition, Longmans/Wiley, New York, 1985). Such methods include vertical spray drying or fluid spray drying and an atomizing means in conjunction with a spray drying chamber through which hot drying gas is circulated.

The atomizing means employed must handle relatively concentrated mixtures and form coarse atomized droplets sufficient in size to contain a plurality of drug particles. Acceptable atomizing means include centrifugal atomizing devices (e.g., see U.S. Pat. Nos. 3,095,149 and 2,814,527) or pressure atomizing devices (e.g., "WhirlJet" manufactured by Spraying Systems Company). A fluidized spray dryer provides a vigorous fluidization of granules in the fluid bed which, together with the recycling of fines (e.g., via a cyclone attachment), results in a granule laden atmosphere for the spray drying to take place.

The resulting spray-dried naproxen or naproxen sodium composition contains granules ranging in particle size from 10 to 500 microns, predominately from 80 to 300 microns. Preferably, the granules range in size from 100 to 150 microns which allows for optimum lubricity when the directly-compressible composition includes pigments. Particle size is determined with a sonic sifter (e.g., Allen-Bradley Sonic Sifter Model 3).

The spray-dried composition is free-flowing, which facilitates handling in automatic equipment (e.g. feeding into high-speed tableting equipment). The bulk density of the spray-dried composition is similar to or higher than that of fine dried drug particles before processing. Thus, in typical instances the bulk density of the spray-dried composition may range from 0.35 to 0.55 grams per mL, whereas the bulk density of drug particles dried by conventional methods range from 0.35 to 0.65 grams per mL. The spray-dried naproxen or naproxen sodium compositions are stable and can be stored in moisture-proof containers for prolonged periods of time.

Spray drying techniques provide maximum drying capacity without causing heat injury to the pharmaceutical. While the inlet air temperatures used in spray drying operations are commonly above the temperatures at which pharmaceuticals decompose, because of the cooling effects of evaporation, the pharmaceutical is subjected to temperatures which are considerably less than the inlet air temperatures.

A spray-dried naproxen or naproxen sodium composition can constitute a directly-compressible composition or the spray-dried composition can be combined with acceptable dry excipients to form a directly-compressible composition. Acceptable excipients include the binders, disintegrating agents, pigments, and lubricants described above. Acceptable excipient levels for a directly-compressible naproxen or naproxen sodium composition are 1 to 6% binder, 1 to 6% disintegrating agent, and 0.1 to 2.0% lubricant.

Naproxen or naproxen sodium compositions must contain acceptable free moisture content to be suitable for direct compression into pharmaceutically acceptable tablets. Tablets compressed from naproxen or naproxen sodium compositions containing higher than acceptable free moisture content do not possess good dissolution characteristics, while naproxen or naproxen sodium compositions containing lower than acceptable free moisture content exhibit poor compressibility and compactibility characteristics. An acceptable free moisture content for a directly-compressible naproxen composition is 0.5 to 1.5%. An acceptable free moisture content for a directly-compressible naproxen sodium composition is 6.0 to 8.0%.

The free moisture content of a naproxen or naproxen sodium composition may be raised by the addition of water or lowered by the addition of dry excipients to the composition, as appropriate. In addition, the free moisture content of a spray-dried composition can be determined by altering the drying conditions during the spray drying process. Drying conditions are altered during the spray drying process by varying the flow of the drying gas and/or by adjusting the inlet temperature of the drying gas and/or by adjusting the temperature of the feed mixture. For example, the inlet temperature of the drying gas may range from 85° to 450° C., preferably from 100° to 300° C.

The directly-compressible naproxen compositions of the present invention consist ,essentially of 90 to 97% spray-dried naproxen, 0.5 to 1.5% free moisture content, 1 to 6% binder, 1 to 6% disintegrating agent, and 0.1 to 2.0% lubricant. Preferred directly-compressible naproxen compositions contain croscarmellose sodium as the disintegrating agent and povidone or hydroxypropylmethylcellulose as a binder. The most preferred directly-compressible naproxen compositions consist essentially of 92 to 96% spray-dried naproxen, 0.5 to 1.5% free moisture ,content, 3 to 5% croscarmellose sodium, 1 to 3% povidone, .and 0.1 to 2.0% lubricant.

The directly-compressible naproxen sodium compositions of the present invention consist essentially of 80 to 90% spray-dried naproxen sodium, 6.0 to 8.0% free moisture .content, 1 to 6% binder, 1 to 6% disintegrating agent, and 0.1 to 2.0% lubricant. Preferred directly-compressible naproxen sodium compositions contain croscarmellose sodium as the disintegrating agent and povidone or hydroxypropylmethylcellulose as a binder. The most preferred directly-compressible naproxen sodium compositions consist essentially of 82 to 86% spray-dried naproxen sodium, 6.0 to 8.0% free moisture content, 2 to 6% croscarmellose sodium, 1 to 4% povidone, and 0.1 to 2.0% lubricant.

The excipient levels and free moisture content of a spray-dried naproxen or naproxen sodium composition should not be greater than that which can be diluted to maximally acceptable amounts for the directly-compressible composition without diluting the naproxen or naproxen sodium below minimally acceptable amounts. Consequently, a spray-dried naproxen composition consists essentially of 90 to 100% naproxen, 0 to 1.63% free moisture content, 0 to 6.25% binder and 0 to 6.25% disintegrating agent. A spray-dried naproxen sodium composition consists essentially of 80 to 100% naproxen sodium, 0 to 9.09% free moisture content, 0 to 6.97% binder, and 0 to 6.97% disintegrating agent.

The solids of an aqueous mixture suitable for spray drying should comprise a sufficient amount of naproxen or naproxen sodium so as to maintain the minimally acceptable amount of naproxen or sodium naproxen when in combination with the acceptable free moisture content of the directly-compressible composition. Consequently, the solids of an aqueous mixture suitable for spray-drying to obtain a spray-dried naproxen composition consist essentially of 90.46 to 100% naproxen, 0 to 6.25% binder, and 0 to 6.25% disintegrating agent. The solids of an aqueous mixture suitable for spray-drying to obtain a spray-dried naproxen sodium composition consist essentially of 85.11 to 100% naproxen sodium, 0 to 6.97% binder, and 0 to 6.97% disintegrating agent.

The directly-compressible naproxen or naproxen sodium compositions prepared from the directly-compressible compositions of the present invention are tableted on a high speed rotary press. The tablets possess good dissolution characteristics which do not substantially decrease with aging.

Tablet dissolution characteristics are determined by recognized in vitro testing procedures. One such procedure is described in *The United States Pharmacopeia XXII*, <711>, page 1578. 22nd ed. Easton: Mack Printing Company, 1990 (i.e., Apparatus 2) and consists of placing the test tablet in a round bottom, 1000 mL vessel containing a dissolution fluid comprised of water, buffer or dilute hydrochloric acid which is maintained at 37° C. and continually stirred by a paddle held in a horizontal position near the bottom of the container. Samples of the dissolution fluid are removed at various intervals and analyzed for concentrations of dissolved drug. The dissolution characteristics determinations for tablets made by the process of the present application are described in Example 2.

Tablet stability characteristics are determined by subjecting the tablets to humid conditions and elevated temperatures (e.g., 93% relative humidity and 40° C.) for prolonged periods of time (e.g., 2 to 12 weeks) and then conducting tests at various intervals to determining solubility characteristics. The stability characteristics for tablets made by the process of the present application are described in Example 2.

Tablets can be film coated with an appropriate polymer (e.g., to serve as an enteric coating or for controlled release of the naproxen or naproxen sodium).

EXAMPLES

The following examples are not intended to limit the scope of the invention. Efforts have been made to insure accuracy with respect to numbers used (e.g., amounts, temperature, etc.) but some experimental errors and deviation should be accounted for.

EXAMPLE 1

PREPARATION OF A DIRECTLY-COMPRESSIBLE NAPROXEN COMPOSITION

In a stainless steel container equipped with a suitable stirrer, naproxen (35.0 Kg) is combined with croscarmellose sodium (1.4 Kg), Povidone K-90 (0.7 Kg) and water (37.1 Kg) to constitute an aqueous mixture comprising 50% solids. Using a Schlick 2-fluid nozzle with a 2.0 mm diameter orifice, the mixture is spray-dried at a nozzle air pressure of 4 psig, main inlet air temperature of 239° C., fluid bed inlet temperature of 88° C. and outlet air temperature of 66° C. to obtain a spray-dried naproxen composition.

Spray-dried naproxen composition is blended with magnesium stearate to produce the following directly-compressible naproxen composition:

| | % |
|---|---|
| Naproxen, USP | 92 |
| Free moisture content | 1.6 |
| Croscarmellose sodium, NF | 4 |
| Povidone K-90, USP | 2 |
| Magnesium Stearate, NF | 0.2 |

The final blend has a mean particle size of 100 to 350 μm, has excellent flow through a hopper and is compressible on a rotary tablet press to 5 S.C. Units under a 600 to 800 pound load and compressible up to 10 to 18 S.C. Units under a 5200 pound compression load.

EXAMPLE 2

APPARATUS 2 (USP PADDLE METHOD) DISSOLUTION TEST

A naproxen tablet is placed in a round bottom, 1000 mL vessel containing 900 mL of phosphate buffer (0.1 M; pH 7.4) prepared by dissolving monobasic sodium phosphate (2.62 g) and anhydrous dibasic sodium phosphate (11.50 g) in 1000 mL of water. The phosphate buffer is maintained at 37° C. and stirred continuously at 50 rpm for 45 minutes.

Samples of the buffer are removed at various intervals, filtered, diluted with fresh phosphate buffer and analyzed for concentrations of naproxen by comparing the ultraviolet absorbance at 332 nm of the test solution to that of a standard solution having a known concentration of USP Naproxen RS.

Approximately 98% of the naproxen dissolves within 5 minutes. No appreciable change in the dissolution rate is observed after storage for four weeks under 93% relative humidity at 40° C.

EXAMPLE 3

PREPARATION OF A DIRECTLY-COMPRESSIBLE NAPROXEN SODIUM COMPOSITION

In a stainless steel container equipped with a suitable stirrer, naproxen sodium (34.6 Kg) is combined with water (65.4 Kg). Using a Schlick 2-fluid nozzle with a 2.0 mm diameter orifice, the mixture is spray-dried at a nozzle air pressure of 4 psig, main inlet air temperature of 179°–186° C., fluid bed inlet temperature of 100°–112° C. and outlet air temperature of 61°–62° C. to obtain a spray-dried naproxen sodium composition.

If necessary, the moisture content of the spray-dried naproxen sodium composition is adjusted to 8.0 to 8.5% and the composition is then blended with other excipients to produce the following directly-compressible naproxen sodium compositions:

| | % |
|---|---|
| Spray-Dried Naproxen Sodium | 82 |
| Free moisture content | 7.5 |
| Croscarmellose sodium, NF | 2 |
| Povidone K-29-32, USP | 3 |
| Talc, USP | 5 |
| Magnesium Stearate, NF | 0.5 |
| Spray-Dried Naproxen Sodium | 82 |
| Free moisture content | 7.5 |
| Croscarmellose sodium, NF | 2 |
| Hydroxypropyl Methylcellulose 2910, USP | 3 |
| Talc, USP | 5 |
| Magnesium Stearate, NF | 0.5 |
| Spray-Dried Naproxen Sodium | 82 |
| Free moisture content | 7.5 |
| Croscarmellose sodium, NF | 4 |
| Povidone K-29-32, USP | 5 |
| Magnesium Stearate, NF | 1.5 |
| Spray-Dried Naproxen Sodium | 82 |
| Free moisture content | 7.5 |
| Croscarmellose sodium, NF | 4 |
| Hydroxypropyl Methylcellulose 2910, USP | 5 |
| Talc, USP | |
| Magnesium Stearate, NF | 1.5 |

Tablets are compressed to a hardness of approximately 10.0 SC Units. When tested by an Apparatus 2 (USP Paddle Method) Dissolution Test, complete dissolution was achieved within 30 minutes.

We claim:

1. A directly-compressible naproxen composition consisting essentially of 90 to 97% spray-dried naproxen, 0.5 to 1.5% free moisture content, 1 to 6% binder, 1 to 6% disintegrating agent, and 0.1 to 2.0% lubricant.

2. The composition of claim 1 in which the disintegrating agent is croscarmellose sodium and the binder is povidone or hydroxypropylmethylcellulose.

3. The composition of claim 2 which consists essentially of 92 to 96% spray-dried naproxen, 3 to 5% croscarmellose sodium, and 1 to 3% povidone.

4. A directly-compressible naproxen sodium composition consisting essentially of 80 to 90% spray-dried naproxen sodium, 6.0 to 8.0% free moisture content, 1 to 6% binder, 1 to 6% disintegrating agent, and 0.1 to 2.0% lubricant.

5. The composition of claim 4 in which the disintegrating agent is croscarmellose sodium and the binder is povidone or hydroxypropylmethylcellulose.

6. The composition of claim 5 which consists essentially of 82 to 86% spray-dried naproxen sodium, 2 to 6% croscarmellose sodium, and 1 to 4% povidone.

7. A process for preparing a naproxen sodium tablet, which process comprises:

(1) spray drying an aqueous mixture-containing 20 to 70% solids, the solids consisting essentially of 85.11 to 100% naproxen sodium, optionally binder in an amount less than or equal to 6.97% and optionally disintegrating agent in an amount less than or equal to 6.97%, to obtain a spray-dried naproxen sodium composition with a free moisture content that does not exceed 9.09%;

(2) combining the spray-dried naproxen sodium composition with sufficient amounts of water and dry excipients to obtain a directly-compressible naproxen sodium composition comprising 80 to 90% spray-dried naproxen sodium, 6.0 to 8.0% free moisture content, 1 to 6% binder, 1 to 6% disintegrating agent, and 0.1 to 2.0% lubricant; and (3) compressing the directly-compressible composition into a tablet.

8. The process of claim 7 in which the naproxen sodium in the aqueous mixture is obtained directly from the final step in the synthesis of the naproxen sodium.

9. The process of claim 8 in which the disintegrating agent is croscarmellose sodium and the binder is povidone or hydroxypropylmethylcellulose.

10. The process of claim 9 in which the directly-compressible composition consists essentially of 82 to 86% spray-dried naproxen sodium, 2 to 6% croscarmellose sodium, and 1 to 4% povidone.

11. A process for preparing a directly-compressible naproxen sodium composition, which process comprises:
   (1) spray drying an aqueous mixture containing 20 to 70% solids, the solids consisting essentially of 85.11 to 100% naproxen sodium, optionally binder in an amount less than or equal to 6.97% and optionally disintegrating agent in an amount less than or equal to 6.97%, to obtain a spray-dried naproxen sodium composition with a free moisture content that does not exceed 9.09%; and
   (2) combining the spray-dried naproxen sodium composition with sufficient amounts of water and dry excipients to obtain a directly-compressible naproxen sodium composition consisting essentially of 80 to 90% spray-dried naproxen sodium, 6.0 to 8.0% free moisture content, 1 to 6% binder, 1 to 6% disintegrating agent, and 0.1 to 2.0 % lubricant.

12. The process of claim 11 in which the naproxen sodium in the aqueous mixture is obtained directly from the final step in the synthesis of the naproxen sodium.

13. The process of claim 12 in which the disintegrating agent is croscarmellose sodium and the binder is povidone or hydroxypropylmethylcellulose.

14. The process of claim 13 in which the directly-compressible composition consists essentially of 82 to 86% spray-dried naproxen, 2 to 6% croscarmellose sodium, and 1 to 4% povidone.

15. An aqueous mixture suitable for spray drying to obtain a spray-dried naproxen composition, the mixture containing 20 to 70% solids, the solids consisting essentially of 90.46 to 100% naproxen, optionally binder in an amount less than or equal to 6.25%, and optionally disintegrating agent in an amount less than or equal to 6.25%.

16. The mixture of claim 15 in which the naproxen is obtained directly from the final step in the synthesis of the naproxen.

17. The mixture of claim 16 in which the disintegrating agent is croscarmellose sodium and the binder is povidone or hydroxypropylmethylcellulose.

18. An aqueous mixture suitable for spray drying to obtain a spray-dried naproxen sodium composition, the mixture containing 20 to 70% solids, the solids consisting essentially of 85.11 to 100% naproxen sodium, optionally binder in an amount less than or equal to 6.97%, and optionally disintegrating agent in an amount less than or equal to 6.97%.

19. The mixture of claim 18 in which the naproxen sodium is obtained directly from the final step in the synthesis of the naproxen sodium.

20. The mixture of claim 19 in which the disintegrating agent is croscarmellose sodium and the binder is povidone or hydroxypropylmethylcellulose.

21. A spray-dried naproxen composition suitable to combine with dry excipients to obtain a directly-compressible naproxen composition, the spray-dried composition consisting essentially of 90 to 100% naproxen, free moisture content that does not exceed 1.63%, optionally binder in an amount less than or equal 6.25% and optionally disintegrating agent in an amount less than or equal 6.25%.

22. The composition of claim 21 having a particle size of 100 to 150 microns.

23. The composition of claim 22 in which the disintegrating agent is croscarmellose sodium and the binder is povidone or hydroxypropylmethylcellulose.

24. A spray-dried naproxen sodium composition suitable to combine with dry excipients to obtain a directly-compressible naproxen sodium composition, the spray-dried composition consisting essentially of 80 to 100% naproxen sodium, free moisture content that does not exceed 9.09%, optionally binder in an amount less than or equal to 6.97% and optionally disintegrating agent in an amount less than or equal to 6.97%.

25. The composition of claim 24 in which contains granules ranging is size from 100 to 150 microns.

26. The composition of claim 25 in which the disintegrating agent is croscarmellose sodium and the binder is povidone or hydroxypropylmethylcellulose.

27. A process for preparing a naproxen tablet, which process comprises:
   (1) combining a spray-dried naproxen composition consisting essentially of 90 to 100% naproxen, free moisture content that does not exceed 1.63%, optionally binder in an amount less than or equal to 6.25%, and optionally disintegrating agent in an amount less than or equal to 6.25% with sufficient amounts of water and dry excipients to obtain a directly-compressible naproxen composition consisting essentially of 90 to 97% spray-dried naproxen, 0.5 to 1.5% free moisture content, 1 to 6% binder, 1 to 6% disintegrating agent, and 0.1 to 2.0% lubricant; and
   (2) compressing the directly-compressible composition into a tablet.

28. The process of claim 27 in which the disintegrating agent is croscarmellose sodium and the binder is povidone or hydroxypropylmethylcellulose.

29. The process of claim 28 in which the directly-compressible composition consists essentially of 92 to 96% spray-dried naproxen, 3 to 5% croscarmellose sodium, and 1 to 3% povidone.

30. A process for preparing a spray-dried naproxen sodium composition suitable to combine with dry excipients to obtain a directly-compressible naproxen sodium composition, which process comprises:
   (1) spray drying an aqueous mixture containing 20 to 70% solids, the solids consisting essentially of 85.11 to 100% naproxen sodium, optionally binder in an amount less than or equal 6.97% and optionally disintegrating agent in an amount less than or equal 6.97%, to obtain a spray-dried naproxen sodium composition with a free moisture content that does not exceed 9.09%.

31. The process of claim 30 in which the naproxen sodium in the aqueous mixture is obtained directly from the final step in the synthesis of the naproxen sodium.

32. The process of claim 31 in which the disintegrating agent is croscarmellose sodium and the binder is povidone or hydroxypropylmethylcellulose.

33. A naproxen tablet consisting essentially of to 97% spray-dried naproxen, 0.5 to 1.5% free moisture content, 1 to 6% binder, 1 to 6% disintegrating agent, and 0.1 to 2.0% lubricant.

34. The tablet of claim 33 in which the disintegrating agent is croscarmellose sodium and the binder is povidone or hydroxypropylmethylcellulose.

35. The tablet of claim 34 which consists essentially of 92 to 96% spray-dried naproxen, 3 to 5% croscarmellose sodium, and 1 to 3% povidone.

36. A naproxen sodium tablet consisting essentially of 80 to 90% spray-dried naproxen sodium, 6.0 to 8.0% free moisture content, 1 to 6% binder, 1 to 6% disintegrating agent, and 0.1 to 2.0% lubricant.

37. The tablet of claim 36 in which the disintegrating agent is croscarmellose sodium and the binder is povidone or hydroxypropylmethylcellulose.

38. The tablet of claim 37 which consists essentially of 82 to 86% spray-dried naproxen sodium, 2 to 6% croscarmellose sodium, and 1 to 4% povidone.

39. A process for preparing a naproxen tablet, which process comprises:
   (1) spray drying an aqueous mixture containing 20 to 70% solids, the solids consisting essentially of 90.46 to 100% naproxen, optionally binder in an amount less than or equal to 6.25% and optionally disintegrating agent in an amount less than or equal 6.25%, to obtain a spray-dried naproxen composition with a free moisture content that does not exceed 1.63%;
   (2) combining the spray-dried naproxen composition with sufficient amounts of water and dry excipients to obtain a directly-compressible naproxen comprising 90 to 97% spray-dried naproxen, 0.5 to 1.5% free moisture content, 1 to 6% binder, 1 to 6% disintegrating agent, and 0.1 to 2.0% lubricant; and
   (3) compressing the directly-compressible composition into a tablet.

40. The process of claim 39 in which the naproxen in the aqueous mixture is obtained directly from the final step in the synthesis of the naproxen.

41. The process of claim 40 in which the disintegrating agent is croscarmellose sodium and the binder is povidone or hydroxypropylmethylcellulose.

42. The process of claim 41 in which the directly-compressible composition consists essentially of 92 to 96% spray-dried naproxen, 3 to 5% croscarmellose sodium, and 1 to 3% povidone.

43. A process for preparing a naproxen sodium tablet, which process comprises:
   (1) combining a spray-dried naproxen sodium composition consisting essentially of 80 to 100% naproxen sodium, free moisture content that does not exceed 9.09%, optionally binder in an amount less than or equal to 6.97%, and optionally disintegrating agent in an amount less than or equal to 6.97% with sufficient amounts of water and dry excipients to obtain a directly-compressible naproxen composition consisting essentially of 80 to 90% spray-dried naproxen sodium, 6.0 to 8.0% free moisture content, 1 to 6% binder, 1 to 6% disintegrating agent, and 0.1 to 2.0% lubricant; and
   (2) compressing the directly-compressible composition into a tablet.

44. The process of claim 43 in which the disintegrating agent is croscarmellose sodium and the binder is povidone or hydroxypropylmethylcellulose.

45. The process of claim 44 in which the directly-compressible composition consists essentially of 82 to 86% spray-dried naproxen sodium, 2 to 6% croscarmellose sodium, and 1 to 4% povidone.

* * * * *